United States Patent [19]

Frey et al.

[11] Patent Number: 4,932,969
[45] Date of Patent: Jun. 12, 1990

[54] JOINT ENDOPROSTHESIS

[75] Inventors: Otto Frey, Winterthur; Rudolf Koch, Berlingen, both of Switzerland; Heinrich M. F. Planck, Nurtigen, Fed. Rep. of Germany

[73] Assignee: Sulzer Brothers Limited, Winterthur, Switzerland

[21] Appl. No.: 134,208

[22] Filed: Dec. 17, 1987

[30] Foreign Application Priority Data

Jan. 8, 1987 [CH] Switzerland ............................ 40/87

[51] Int. Cl.⁵ .............................................. A61F 2/44
[52] U.S. Cl. ......................................... 623/17; 623/18
[58] Field of Search ................. 623/7, 8, 11, 12, 17, 623/16, 18

[56] References Cited

U.S. PATENT DOCUMENTS

| 3,867,728 | 2/1975 | Stubstad et al. | 623/17 |
| 3,875,595 | 4/1975 | Froning | 623/17 |
| 4,205,401 | 6/1980 | Frisch | 623/8 |
| 4,707,872 | 11/1987 | Hessel | 5/451 |
| 4,772,287 | 9/1988 | Ray et al. | 623/17 |

FOREIGN PATENT DOCUMENTS

| 0179695 | 4/1986 | European Pat. Off. |
| 2263842 | 7/1974 | Fed. Rep. of Germany |
| 2372622 | 6/1978 | France |

*Primary Examiner*—David J. Isabella
*Attorney, Agent, or Firm*—Kenyon & Kenyon

[57] ABSTRACT

The joint endoprosthesis is formed of a compressible elastic hollow body which is disposed between two anchoring elements. The hollow body defines a closed cavity which is filled with an incompressible fluid medium. Compressive loadings near the edges of the endoprosthesis cause a displacement of the liquid into relieved regions of the prosthesis so as to avoid tensile forces from occurring in the anchoring of the prosthesis to the bones.

9 Claims, 2 Drawing Sheets

JOINT ENDOPROSTHESIS

This invention relates to a joint endoprosthesis. More particularly, this invention relates to a joint endoprosthesis which can be used as an intervertebral prosthesis.

German O.S. No. 2263842 describes a joint endoprosthesis which can be used as an intervertebral prosthesis. In this regard, the prosthesis consists of two hard, metal bearing shells between which an elastic intermediate layer of silicone rubber is disposed. In addition, in order to reduce the compressibility of the prosthesis in the axial direction, i.e. in the direction of the spinal column, a spacer element is provided in the center of the intermediate layer which is either a little elastic or not at all. Optionally, this spacer element may also consist of a harder region of the intermediate layer. However, due to the "central fulcrum" formed by the incompressible spacer element, undesirable tensile stresses may occur under loads near the edge in the region of the prosthesis opposite the stressing part of the edge beyond the "center of rotation". The stresses may, in turn, result in loosening or even detachment of the prosthesis at the boundries between the vertebrae and the hard prosthesis shell.

French Patent No. 2,372,622 describes an intervertebral prosthesis which consists of a central ball which has a plate integrated in an equatorial region with a thickness approximately corresponding to the thickness of an intervertebral disk. This prosthesis is made of plastic with the plate being undeformable and incompressible while the central ball consists of an easily deformable but also incompressible medium. With this construction, it is practically not possible for the prosthesis to yield under edge loads. Thus, vertebrae between which the prosthesis is implanted have practically no possibility, because of the undeformable plate, "to come closer" to each other in the stressed edge region.

Accordingly, it is an object of the invention to provide a prosthesis in which undesired tensile stresses under unilateral loads on its edge are reduced or completely avoided.

It is another object of the invention to provide a joint endoprosthesis which can be readily used as an intervertebral prosthesis.

It is another object of the invention to provide a compressible endoprosthesis which is able to accept edge loadings without becoming loosened.

Briefly, the invention provides a joint endoprosthesis which is comprised of an elastic compressible elastic hollow body defining at least one closed cavity therein, an incompressible fluid medium filling the cavity and anchoring elements on the body for securing the body between and to two bones.

With a fluid medium which is incompressible under the occurring loads, the elastic compressible hollow body maintains a constant volume. Under "decentralized" loads, the liquid content in the cavity of the hollow body shifts to a load-remote region of the body and leads to an expansion of the body in that region. Thus, tensile stresses are reduced or even avoided.

Where the endoprosthesis is placed between two adjacent vertebrae, movements of these vertebrae relative to each other causes the "axis of rotation" to migrate through the entire of volume of fluid in accordance with the momentary local compressive stress.

The transverse stability of the prosthesis can be improved by subdividing the cavity into several intercommunicating chambers via partitions provided with passage openings. If the transverse stability obtained with the partitions should be insufficient, a construction of high transverse stability will result if the hollow body is formed as a toroidal ring with an annular cavity filled with an incompressible fluid medium and if the body is mounted between shells which are contoured as a negative form thereof.

An especially intimate connection of the anchoring elements with the contiguous vertebrae can be achieved if the anchoring elements are formed as metal grids of several layers. Furthermore, excessive expansion of the hollow body in a radial direction under compressive stress can be limited if the radial limit of the body, at least, is reinforced by a reinforcing means.

The anchoring elements may be made predominately of metal, particularly of titanium or titanium alloys while the hollow body is formed of a highly elastic polymer, for example, a polyurethane. The fluid medium may be a suitable body-compatible liquid, for example a physiological common salt solution or, if a higher viscosity is desired, a silicone oil.

These and other objects and advantages of the invention will become more apparent from the following detailed description taken in conjunction with the accompanying drawings wherein.

Figure 1:
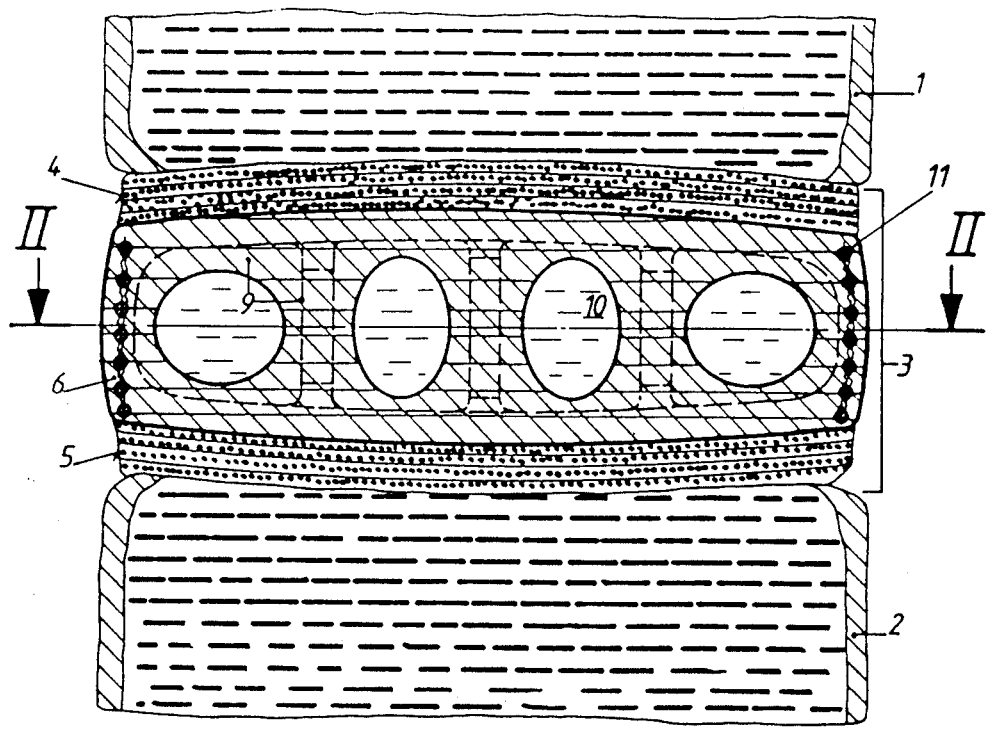
FIG. 1 illustrates a cross-sectional view taken on line I—I of FIG. 2 of an axial section of a joint endoprosthesis constructed in accordance with the invention.

Referring to FIG. 1, the joint endoprosthesis 3 is constructed for use as an intervertebral prosthesis for implantation between two vertebral bodies 1, 2.

The endoprosthesis 3 includes a pair of anchoring elements 4, 5 which are formed as bearing shells consisting of multiple layers of wire mesh, for example of pure titanium or a titanium alloy. The "open-cell" outer layers of the anchoring elements 4, 5 serve to connect the prosthesis 3 with the vertebral bodies 1, 2 by an ingrowth of bone tissue.

The prosthesis 3 also includes an elastic compressible hollow body 6 which is sandwiched between the anchoring elements 4, 5 and which consists of a compressible plastic, for example polyurethane.

The surfaces of the anchoring elements 4, 5 are porous because of their reticular structure and are anchored in the hollow body 6 with at least one layer of the mesh embedded in the plastic of the body 6 in known manner, for example, as described in copending U.S. patent application Ser. No. 06/816,340, filed Jan. 6, 1986.

Figure 2:
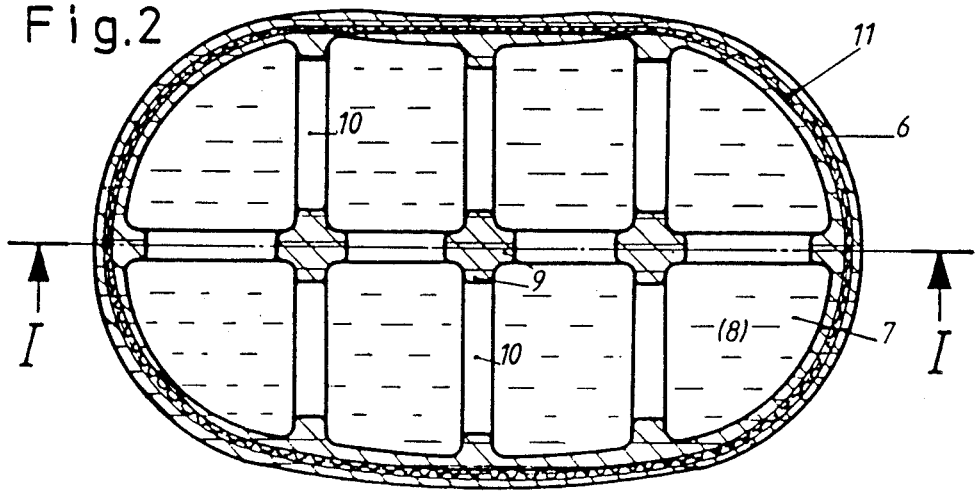
FIG. 2 illustrates a view taken on line II—II of FIG. 1.

As indicated in FIG. 1, the body 6 forms a cushion between the two anchoring elements. In addition, the body 6 is provided with a closed cavity which is filled with an incompressible fluid medium 8. As indicated in FIGS. 1 and 2, in order to increase transverse stability of the hollow body 6, the closed cavity is subdivided by a plurality of partitions 9 e.g. eight cavities. In addition, passage openings are provided in the partitions 9 to communicate the cavities with each other so that the incompressible fluid medium 8 is free to move from cavity to cavity to effect liquid equalization between stressed and unstressed cavities during stressing.

The fluid medium 8 may, for instance, be a body-compatible liquid, such as physiological sodium chloride or a silicon oil. The latter media has the advantage that by selecting amongst several oils, the viscosity of the cavity filling may be varied within certain limits. The possibility for varying viscosity is also offered by an ethylenoxide-propylenoxide-copolymer, where the molecular weight and the portions of the two polymers may be changed within wide ranges.

As indicated in FIG. 2, the body 6 is somewhat elliptical in shape and is provided with a circumferentially disposed reinforcing means 11 to prevent excessive expansion of the body 6 in a radial direction under compressive stresses or undesired radial turning of the body 6. Any suitable reinforcing means may be used for this purpose and may be made of a tissue, knitting or plaid or weave or of plies. Suitable materials are for instance synthetic or hydrocarbon fibers in mono- or multi-filament form with a suitable mechanical stability and stiffness.

When the prosthesis 3 is implanted between two vertebrae bodies 1, 2, the fluid filled body 6 is at least approximately incompressible in the axial direction. In this regard, should an edge loading be placed on the prosthesis 3, for example, at the right-hand edge as viewed in FIG. 1, the hollow body 6 will compress slightly at that point while expanding at the left-hand side.

Figure 3:
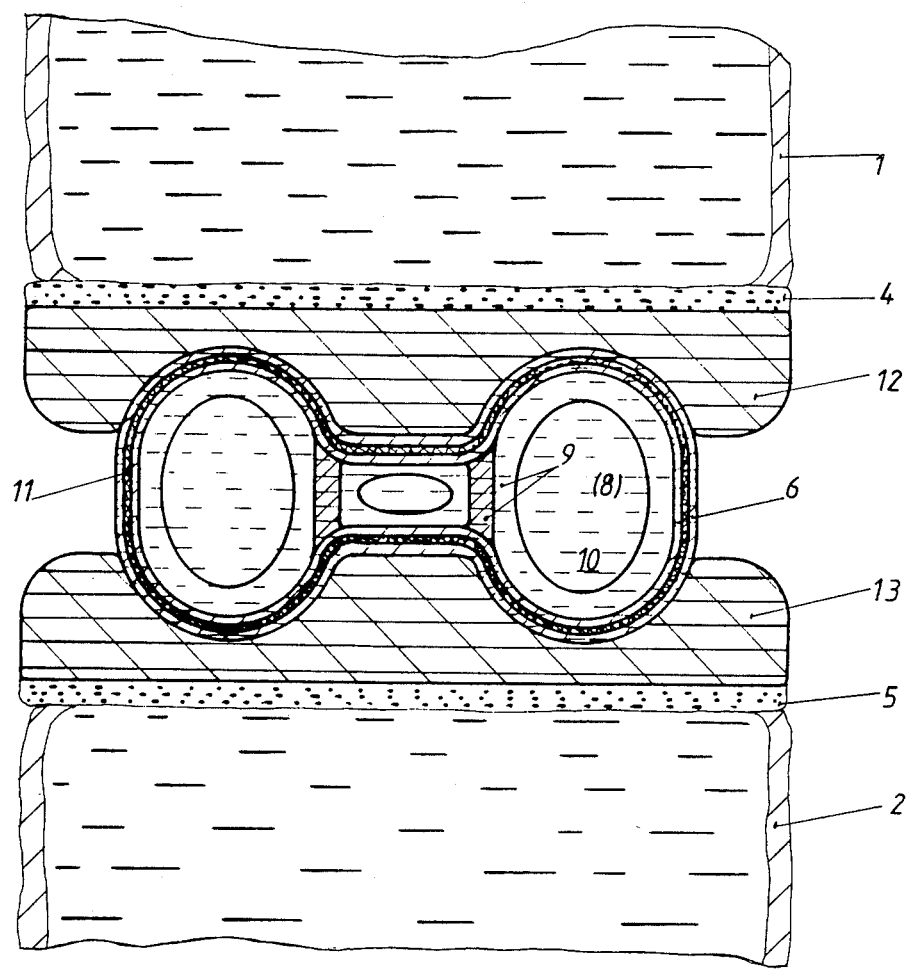
FIG. 3 illustrates a modified joint endoprosthesis constructed in accordance with the invention.

Referring to FIG. 3, wherein like reference characters indicate like parts as above, the endoprosthesis may have a hollow body 6 in the form of a toroidal ring which defines an annular cavity for the incompressible fluid medium 8. In addition, a pair of contoured shells 12, 13 matingly receive the body 6 therebetween with the anchoring elements 4, 5 provided to the exterior of the shelves 12, 13.

In this embodiment, the multi-layer metal grids which form the anchoring elements 4, 5 are not directly connected with the elastic hollow body 6 but are fastened to the shells 12, 13 which consist of a plastic common in implant technology.

As illustrated, the interior of the hollow body 6 is bridged by a flow cavity for the fluid medium 8 so that the medium may not only circulate in the annular cavity but may also flow diametrically through the toroidal ring. This flow cavity communicates via oppositely disposed openings 10 in the annular partition 9 with the annular cavity.

In order to stabilize the hollow body 6 in the transverse direction, the shells 12, 13 are contoured as a negative form thereof.

As above, the hollow body 6 is provided with a reinforcing means 11 in order to increase its "internal" stability. As indicated, this reinforcement means is not only circumferentially disposed about the toroidal ring 6 but also extends through the top and bottom surfaces. This embodiment has an increased transverse stability relative to the FIG. 1 embodiment such that "swimming" of the verterbral bodies 1 toward one another is kept within narrow limits.

In each of the above described embodiments, the flow of medium 8 in each hollow body is damped and delayed by the partitions 9 with the openings therein providing throttle-like passages.

The endoprosthesis may serve not only as an intervertebral prosthesis but also in the replacement of other joints such as a wrist prosthesis.

The invention thus provides a joint endoprosthesis which is able to react to edge loadings without imposing tensile stresses in other regions of the prosthesis.

The invention further provides a joint endoprosthesis for positioning between two bones which has an enhanced transverse stability.

What is claimed is:

1. A joint endoprosthesis comprising
an elastic compressible hollow body having a plurality of partitions defining a plurality of cavities therein and passage openings in said partitions communicating said cavities;
an incompressible body-compatible fluid medium filling said, said medium being selected from the group consisting of physiological sodium chloride and silicon oil and being free to move from cavity to cavity to effect liquid equalization between stressed and unstressed cavities during stressing; and
anchoring elements on said body for securing said body between and to two bones.

2. A joint endoprosthesis as set forth in claim 1 wherein each anchoring element is a multi-layer metal grid.

3. A joint endoprosthesis as set forth in claim 1 which further comprises a circumferentially disposed reinforcing means in said body.

4. A joint endoprosthesis as set forth in claim 1 wherein said body is a toroidal ring and said cavities include an annular cavity.

5. A joint endoprosthesis as set forth in claim 4 which further comprises a pair of contoured shells matingly receiving said body therebetween.

6. An intervertebral endoprosthesis for implantation between two vertebral bodies comprising
an elastic compressible hollow body having a plurality of partitions defining a plurality of cavities therein and passage openings in said partitions communicating said cavities therein;
an incompressible body-compatible fluid medium filling said cavities to render said body at least approximately incompressible in an axial direction thereof wherein under a decentralized load said fluid medium is free to move from cavity to cavity to effect liquid equalization between stressed and unstressed cavities during stressing whereby said fluid medium shifts to a load remote region of said body for expansion thereof to reduce tensile stresses thereat; and
anchoring elements on said body for securing said body between and to two vertebral bodies.

7. An endoprosthesis as set forth in claim 6 which further comprises a circumferentially disposed reinforcing means in said body.

8. An endoprosthesis as set forth in claim 6 wherein said body is a toroidal ring and said cavities include an annular cavity and a flow cavity bridging said annular cavity and communicating therewith for diametric flow of said fluid medium therethrough.

9. An endoprosthesis as set forth in claim 6 wherein said fluid medium is a salt solution.

* * * * *

UNITED STATES PATENT AND TRADEMARK OFFICE
CERTIFICATE OF CORRECTION

PATENT NO.   : 4,932,969
DATED        : June 12, 1990
INVENTOR(S)  : OTTO FREY, et al It is certified that error appears in the above-identified patent and that said Letters Patent is hereby corrected as shown below:

```
Column 1, line 67 change "entire of volume" to -entire volume-
Column 4, line 17 after "said" (first occurrence) insert
      -cavities-
```

Signed and Sealed this

Eighteenth Day of February, 1992

Attest:

HARRY F. MANBECK, JR.

*Attesting Officer*       Commissioner of Patents and Trademarks